(12) United States Patent
Brown et al.

(10) Patent No.: US 8,563,794 B2
(45) Date of Patent: *Oct. 22, 2013

(54) EXTENDING THE LIFE OF AN AROMATIZATION CATALYST

(75) Inventors: Scott H. Brown, Kingwood, TX (US); Tin-Tack Peter Cheung, Kingwood, TX (US); Daniel P. Hagewiesche, Carlsbad, CA (US); Baiyi Zhao, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/614,980

(22) Filed: Sep. 13, 2012

(65) Prior Publication Data

US 2013/0066125 A1 Mar. 14, 2013

Related U.S. Application Data

(60) Continuation of application No. 12/962,250, filed on Dec. 7, 2010, now Pat. No. 8,288,603, which is a division of application No. 11/940,115, filed on Nov. 14, 2007, now Pat. No. 7,868,217.

(51) Int. Cl.
*C07C 2/52* (2006.01)

(52) U.S. Cl.
USPC ............ 585/418; 585/420; 585/904; 585/906

(58) Field of Classification Search
USPC .................................. 585/418, 420, 904, 906
See application file for complete search history.

(56) References Cited

U.S. PATENT DOCUMENTS

| | | |
|---|---|---|
| 2,882,244 A | 4/1959 | Milton |
| 3,130,007 A | 4/1964 | Breck |
| 3,216,789 A | 11/1965 | Breck et al. |
| 3,267,026 A | 8/1966 | Decker |
| 4,021,447 A | 5/1977 | Rubin et al. |
| 4,071,439 A | 1/1978 | Yanik et al. |
| 4,503,023 A | 3/1985 | Breck et al. |
| 4,539,304 A | 9/1985 | Field |
| 4,539,305 A | 9/1985 | Wilson et al. |
| 4,937,215 A | 6/1990 | Murakawa et al. |
| 5,073,529 A | 12/1991 | Miller et al. |
| 5,138,108 A | 8/1992 | Tustin et al. |
| 5,155,075 A | 10/1992 | Innes et al. |
| 5,723,707 A | 3/1998 | Heyse et al. |
| 5,863,418 A | 1/1999 | Heyse et al. |
| 5,883,031 A | 3/1999 | Innes et al. |
| 5,895,636 A | 4/1999 | Nguyen et al. |
| 6,207,120 B1 | 3/2001 | Belmonte et al. |
| 6,812,180 B2 | 11/2004 | Fukunaga |
| 7,153,801 B2 | 12/2006 | Wu |
| 7,582,272 B2 | 9/2009 | Glova et al. |
| 7,868,217 B2 | 1/2011 | Brown et al. |
| 8,288,603 B2 | 10/2012 | Brown et al. |

FOREIGN PATENT DOCUMENTS

| | | |
|---|---|---|
| EP | 0498187 B1 | 8/1992 |
| WO | 9209367 A1 | 6/1992 |
| WO | 9215654 A1 | 9/1992 |
| WO | 9402246 A1 | 2/1994 |
| WO | 2005089923 A1 | 9/2005 |
| WO | 2009064620 A2 | 5/2009 |
| WO | 2009064620 A3 | 5/2009 |

OTHER PUBLICATIONS

CP Chem editorial, plus respiratory (benzene), "Statement of commitment to responsible care®," Jun. 2003, pp. i, ii, iii, and 1-25, Aromatics Customer Technical Service Group, Chevron Phillips Chemical Company LP.

Figoli, N.S., et al., "Accelerated deactivation tests in naphtha reforming, Applied Catalysis," 1986, pp. 39-45, vol. 26, Elsevier Science Publishers B.V., Amsterdam.

Foreign communication from a related counterpart application— International Search Report and Written Opinion, PCT/US2008/081826, Aug. 31, 2009, 16 pages.

Foreign communication from a related counterpart application— International Preliminary Report on Patentability, PCT/US2008/081826, May 27, 2010, 9 pages.

Foreign communication from a related counterpart application— Chinese Office Action, Application No. 2008801223381, Jan. 31, 2012, 9 pages.

Foreign communication from a related counterpart application— Chinese Office Action, Application No. 2008801223381, Aug. 31, 2012, 4 pages.

(Continued)

*Primary Examiner* — Thuan D Dang
(74) *Attorney, Agent, or Firm* — Rodney B. Carroll; Chad E. Walter (57) ABSTRACT

A method of extending the life of an aromatization catalyst comprising identifying a rapid deactivation threshold (RDT) of the catalyst, and oxidizing the catalyst prior to reaching the RDT. A method of aromatizing a hydrocarbon comprising identifying a rapid deactivation threshold (RDT) for an aromatization catalyst, and operating an aromatization reactor comprising the catalyst to extend the Time on Stream of the reactor prior to reaching the RDT. A method of extending the life of an aromatization catalyst comprising predicting a rapid deactivation threshold (RDT) for an aromatization reactor by employing the catalyst in a reactor system under an accelerated fouling condition to identify a test rapid deactivation threshold (t-RDT), predicting the RDT for the aromatization reactor based upon the t-RDT, and oxidizing the catalyst prior to the predicted RDT to extend the Time on Stream of the aromatization catalyst.

13 Claims, 8 Drawing Sheets

(56) References Cited

OTHER PUBLICATIONS

Li, Yonggang, et al., "Combined single-pass conversion of methane via oxidative coupling and dehydro-aromatization," XP-002541956, Catalysis Letters, Nov. 2005, vol. 105, Nos. 1-2, pp. 77-82, Springer Science + Business Media.

Logan, Jr., H. H., et al., "Catforming at united refining company," XP008047473, Sep. 1955, pp. 169-173, vol. 34, No. 9, Petroleum Refiner.

Schneider, D. F., "Improve catalyst removal methods," XP-000969611, Oct. 2000, pp. 39-42, Hydrocarbon Processing.

Stamey, D. J., et al., "Inert entry cuts delay, solves catalyst problems," XP008047398, Mar. 28, 1977, pp. 64-68, The Oil and Gas Journal.

Foreign communication from a related counterpart application—International Search Report and Written Opinion, PCT/US2005/008028, Jun. 1, 2005, 11 pages.

Foreign communication from a related counterpart application—European Examination Report, Application No. 08 850 031.9, May 25, 2012, 8 pages.

Foreign communication from a related counterpart application—International Preliminary Report on Patentability, PCT/US2005/008028, Jul. 13, 2006, 11 pages.

Foreign communication from a related counterpart application—Japanese Office Action Translation, JP Patent Application No. 2010-534091, Dec. 25, 2012, 9 pages.

EXTENDING THE LIFE OF AN AROMATIZATION CATALYST

CROSS-REFERENCE TO RELATED APPLICATIONS

This application is a continuation of and claims priority to U.S. patent application Ser. No. 12/962,250, filed Dec. 7, 2010 and published as U.S. Publication No. 2011/0190558 A1, and entitled "Extending the Life of an Aromatization Catalyst," which was a Divisional application of U.S. patent application Ser. No. 11/940,115 filed Nov. 14, 2007, now U.S. Pat. No. 7,868,217 B2, and entitled "Extending the Life of an Aromatization Catalyst," which is hereby incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present disclosure generally relates to aromatization of hydrocarbons with an aromatization catalyst. More specifically, the disclosure relates to extending the life of an aromatization catalyst by identifying a rapid deactivation threshold of the catalyst and oxidizing the catalyst prior to reaching the rapid deactivation threshold.

BACKGROUND OF THE INVENTION

Catalyzed reactions and associated catalytic reactor systems are widely used in a variety of industries. A catalyst typically has a finite performance life, which may include one or more cycles of catalyst activity separated by regeneration cycles. For example, as a catalytic process continues over time, the catalyst activity generally decreases. When the catalyst activity reaches a point at which it no longer efficiently catalyzes the process, the catalyst may be at the end of its life or at the end of one of its cycles of catalyst activity. If the catalyst has one or more cycles of catalyst activity remaining, the catalyst can be regenerated to begin a new cycle of catalyst activity. If no additional cycles are available, the catalyst life is spent, and the spent catalyst typically will need to be replaced with fresh catalyst. Increasing the length of the catalyst cycle and/or increasing the number of cycles may significantly improve the overall economics of the catalyzed process. Consequently, an ongoing need exists for improved methods for extending the life of a catalyst.

SUMMARY OF THE INVENTION

Disclosed herein is a method of extending the life of an aromatization catalyst comprising identifying a rapid deactivation threshold (RDT) of the catalyst, and oxidizing the catalyst prior to reaching the RDT.

Also disclosed herein is a method of aromatizing a hydrocarbon comprising identifying a rapid deactivation threshold (RDT) for an aromatization catalyst, and operating an aromatization reactor comprising the catalyst to extend the Time on Stream of the reactor prior to reaching the RDT.

Further disclosed herein is a method of characterizing an aromatization catalyst comprising identifying a rapid deactivation threshold (RDT) of the catalyst.

Further disclosed herein is a method of extending the life of an aromatization catalyst comprising predicting a rapid deactivation threshold (RDT) for an aromatization reactor by employing the catalyst in a reactor system under an accelerated fouling condition to identify a test rapid deactivation threshold (t-RDT), predicting the RDT for the aromatization reactor based upon the t-RDT, and oxidizing the catalyst prior to the predicted RDT to extend the Time on Stream of the aromatization catalyst.

Further disclosed herein is a method of aromatizing a hydrocarbon comprising contacting a hydrocarbon with an aromatization catalyst comprising a crystalline aluminosilicate within a commercial-scale aromatization reactor to produce aromatic hydrocarbons, employing the aromatization catalyst in a test reactor system under an accelerated fouling condition to identify a test rapid deactivation threshold (t-RDT), predicting a rapid deactivation threshold (RDT) for the aromatization catalyst based upon the t-RDT, and oxidizing the catalyst prior to the predicted RDT to extend the Time on Stream of the aromatization catalyst.

DETAILED DESCRIPTION

The life of a catalyst may be extended by identifying a rapid deactivation threshold (RDT) of the catalyst. The RDT may be identified by locating a point or temperature range on a catalyst fouling curve where the fouling rate of the catalyst becomes non-linear. Upon identifying the RDT, the catalyst is oxidized prior to reaching the RDT. An example of a suitable catalyst includes without limitation an aromatization catalyst comprising a Group VIII metal and one or more halides on an inorganic support. The methods disclosed herein may be employed in a process for aromatizing hydrocarbons to extend the life of an aromatization catalyst. The remainder of the detailed description is directed to aromatization catalysts and processes, with the understanding the methods and techniques described herein may be applied to other catalysts and related processes as will be apparent to those skilled in the art.

Figure 1:
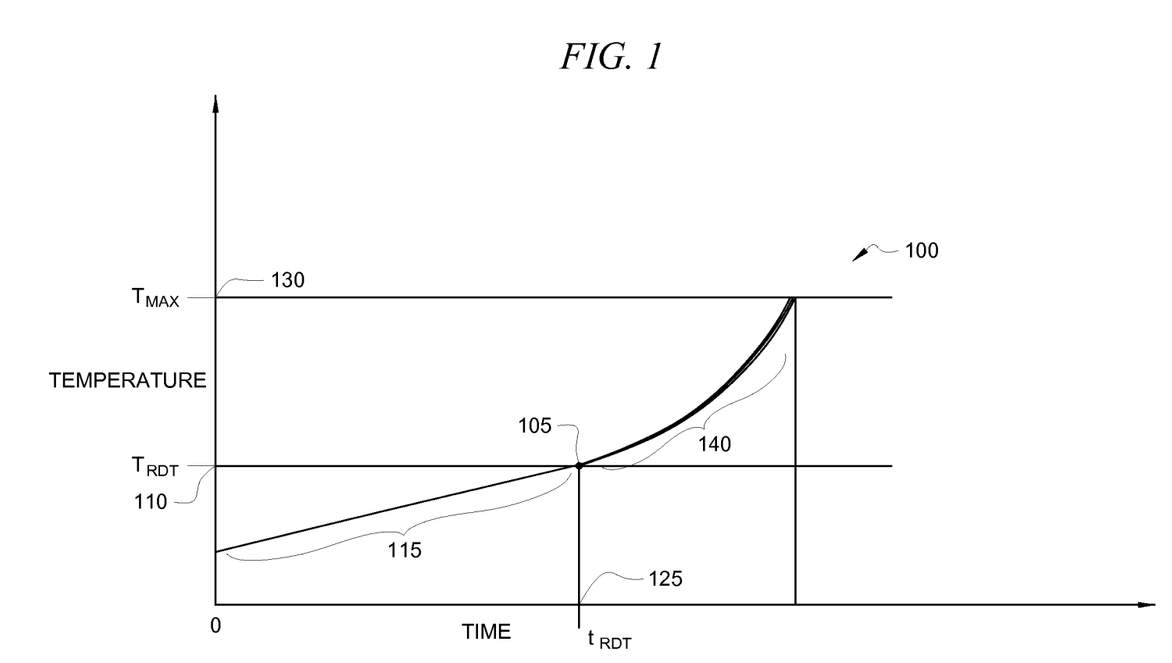
FIG. 1 is a graph of a fouling curve showing a rapid deactivation threshold.

A catalyst fouling curve, sometimes referred to as a fouling profile, may be used to identify a RDT of a catalyst. Referring to FIG. 1, a catalyst-fouling curve 100 is obtained by plotting the yield-adjusted temperature of the catalyst as a function of Time on Stream (TOS). The slope of the plot is positive and represents increases in the reactor and catalyst temperature necessary to maintain a constant product yield. The yield-adjusted temperature may also be referred to as the "normalized temperature" or $T_{norm}$. As will be understood by one of ordinary skill in the art, the specific definition of $T_{norm}$ will depend on a variety of reactions conditions such as for example the number of reactors employed in a given system and the specific target yield chosen. In an embodiment, $T_{norm}$ may be the temperature of an isothermal or adiabatic catalyst bed. Alternatively, $T_{norm}$ may be the catalyst temperature normalized to a specific level of catalyst productivity at a defined set of process conditions. Alternatively, $T_{norm}$ for an aromatization process may be the isothermal furnace set point temperature, corrected to a specific target yield of % aromatics in the overall product stream. This furnace set point temperature is normally the same as the bed inlet temperature. Alternatively, $T_{norm}$ for an adiabatic aromatization process may be the reactor inlet set point temperature, corrected for differences from a specific target yield of % aromatics in the overall product stream.

Time on Stream (TOS) as used herein refers to the amount of time that the catalyst is in use in a given process, or stated alternatively the time that the catalyst is in contact with reactants under effective process conditions for catalyzing the reaction. The slope of the plotted line represents the fouling rate of the catalyst in degrees Fahrenheit per hour (° F./hr). The fouling curves are further defined by the reaction conditions at which the catalyst was used and the data was gathered.

In an alternative embodiment, a catalyst-fouling curve may be prepared wherein the normalized catalyst activity is plotted as a function of Time on Stream. In such an embodiment, the fouling curve generated would be the inverse shape of fouling curves generated using $T_{norm}$ data.

The catalyst-fouling curve may be prepared by plotting data gathered over the life of the catalyst, for example data gathered during the actual, real-time use of a catalyst on an experimental, pilot, or commercial scale. However, gathering such actual use data may take several months depending upon the life of a particular catalyst. Thus, the catalyst-fouling curve may also be prepared by plotting data gathered from using the catalyst under one or more accelerated fouling conditions (AFC). An AFC may be achieved by adjusting one or more reaction conditions to increase the rate at which the catalyst fouls. Examples of AFCs include an elevated reaction pressure, a decrease in hydrogen to hydrocarbon mole ratio, an elevated hydrocarbon flow per unit of catalyst, or any combination thereof. In an embodiment, the catalyst is operated under an AFC in a test reactor system, for example a lab scale reactor system, to identify a test rapid deactivation threshold (referred to herein as t-RDT). The RDT for a commercial scale aromatization reactor may thus be predicted based upon the t-RDT determined under AFCs. In further embodiments, a catalyst in an operating, commercial-scale aromatization reactor is oxidized based on the RDT predicted by a t-RDT, as described in more detail herein. Such oxidation based on the RDT predicted by the t-RDT may extend the Time on Stream of the catalyst in a commercial reactor. Hereinafter, the initial catalyst activity in the AFC test reactor system may be expressed as the "t-SOR" and describe the initial temperature needed in the AFC to achieve target conversion. Furthermore, the initial fouling rate determined in the AFC test reactor system may be designated t-FR while the t-TOS is the run length under AFC or the number of hours the catalyst operated at AFC in the test reactor system before target conversion could no longer be achieved. Thus, the designation of a catalytic property Z, as a t-Z indicates the property was determined in the laboratory reactor system under AFC as opposed to a commercial system.

Referring to FIG. 1, the catalyst-fouling curve 100 comprises a linear fouling portion 115 and a non-linear fouling portion 140. In the linear fouling portion 115, the slope of the curve (i.e., the fouling rate) is about constant. In the non-linear fouling portion 140, the slope of the curve (i.e., the fouling rate) is changing. The fouling rate represents the change in catalyst activity over a given period of time, expressed in degrees Fahrenheit per hour (° F./hr). The non-linear fouling portion 140 may represent an increasing fouling rate for the catalyst, which may increase about exponentially for some catalysts. Thus, the non-linear fouling portion 140 may correspond to rapid deactivation of the catalyst. The point or temperature range on the catalyst fouling curve where the fouling rate transitions from linear to non-linear behavior is referred to as the RDT 105 of the catalyst. The maximum temperature, $T_{max}$ as indicated by reference numeral 130, represents the maximum operating temperature of the catalyst, which may be defined by process considerations such as reactor design limits, etc. Typically, the RDT temperature is less than the $T_{max}$.

Figure 4:
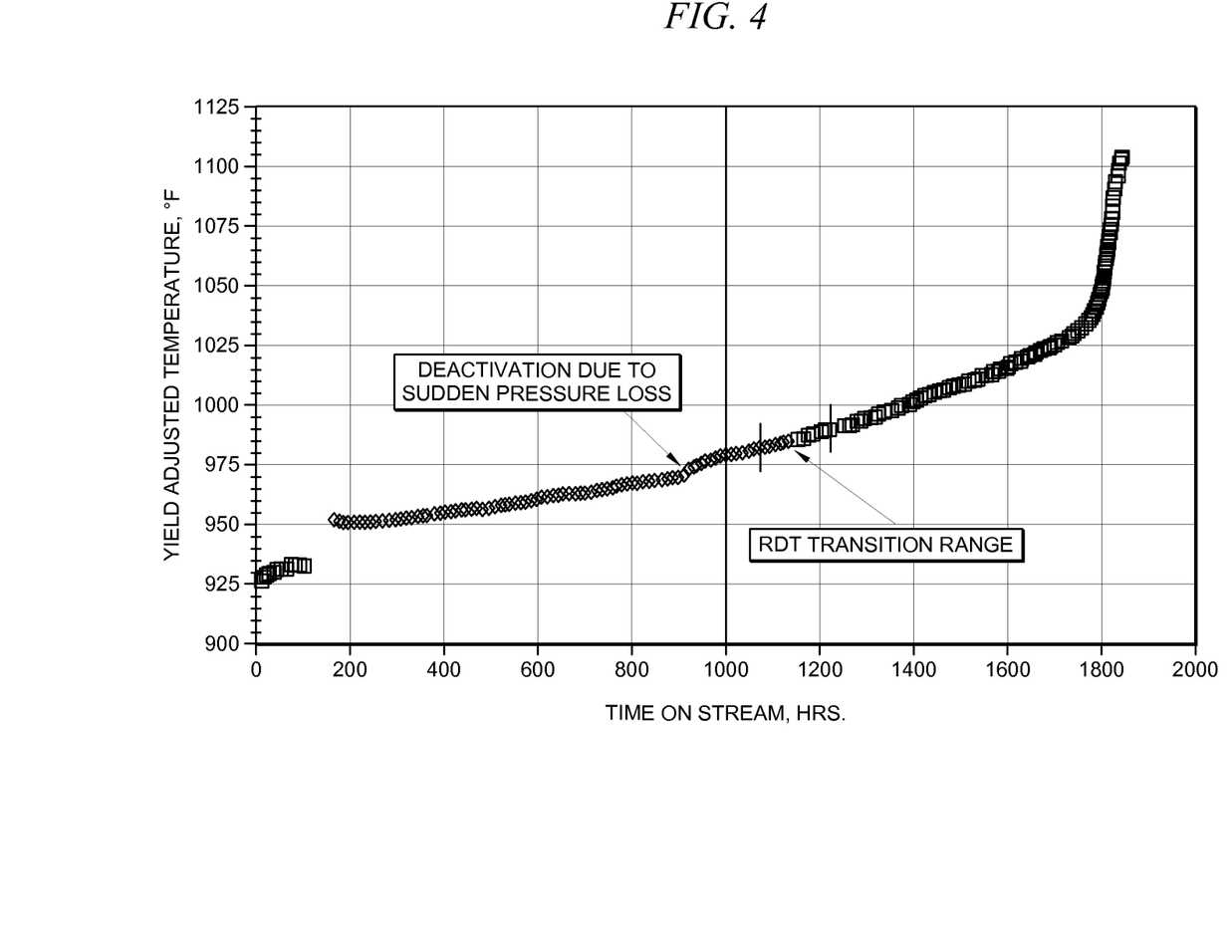
FIGS. 4-8 are fouling curves for catalysts used in the Examples.
Figure 7:
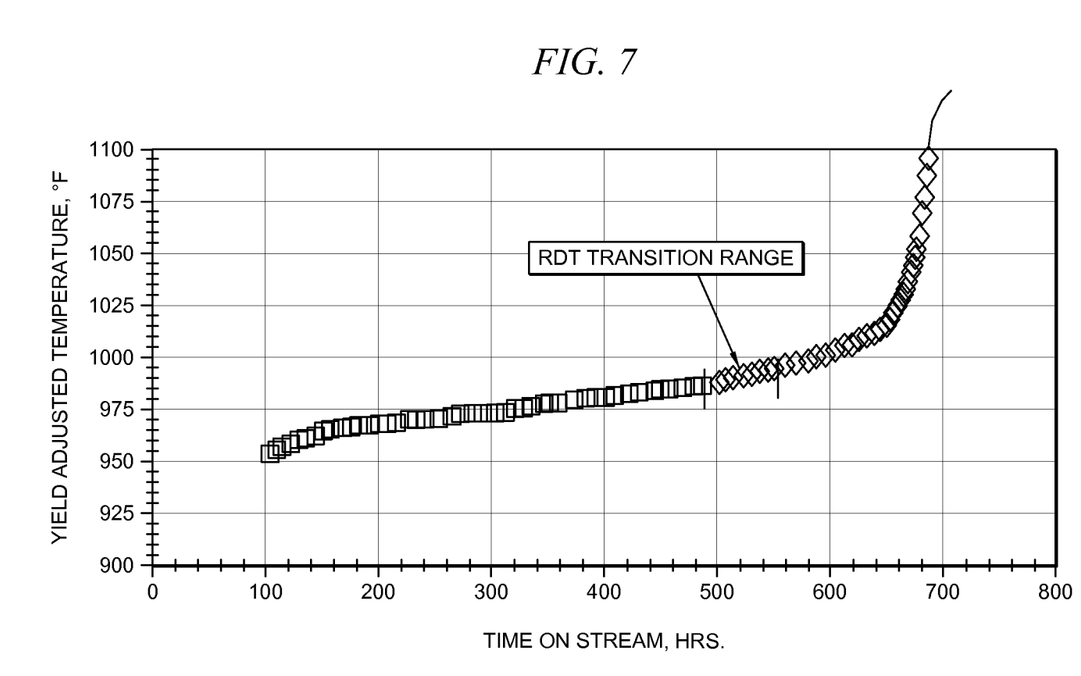

The RDT may correspond to a specific temperature, referred to as the RDT temperature ($T_{RDT}$) 110, at which the catalyst transitions from a linear fouling rate to a non-linear fouling rate. Alternatively, the RDT may correspond to a range in temperature, which may be referred to as an RDT temperature transition range, as is shown in FIGS. 4 and 7 and discussed in more detail herein. Likewise, the RDT may correspond to a specific time or a range in time, referred to as the RDT time 125, within which the catalyst transitions from a linear fouling rate to a non-linear fouling rate. The RDT may also correspond to other characteristics or properties of the catalyst. For example, the RDT may correspond to the halogen content of the catalyst, as described in more detail herein. In embodiments, identifying the catalyst RDT comprises identifying a point or temperature range on a catalyst fouling curve at which the fouling rate of the catalyst becomes non-linear as a function of Time on Stream. In some embodiments, identifying the RDT comprises identifying a point or temperature range on a catalyst fouling curve at which the fouling rate of the catalyst becomes non-linear as a function of reactor temperature, or yield adjusted reactor temperature. In other embodiments, identifying the RDT comprises identifying a point or temperature range on a catalyst fouling curve at which the fouling rate of the catalyst becomes non-linear as a function of a halogen content of the catalyst. In yet further embodiments, identifying the RDT may comprise identifying a point or temperature range on a catalyst fouling curve at which the fouling rate of the catalyst becomes non-linear as a function of any combination of Time on Stream, reactor temperature, and halogen content.

Identifying the RDT may further comprise identifying a minimum amount of halogen required in the catalyst to inhibit catalyst deactivation during aromatization. The temperature employed during any oxidative regeneration of the catalyst may be sustained such that the level of halogen on the catalyst is maintained above the minimum amount. In certain embodiments, catalyst halogen content is based on fluoride content, chloride content, or combinations thereof. In an embodiment, a minimum amount of fluoride present in the catalyst is from about 0.05 to about 0.30 weight percent; alternatively, from about 0.05 to about 0.20 weight percent; or alternatively, from about 0.10 to about 0.15 weight percent.

As noted previously, the catalyst-fouling rate may be dependent upon the underlying reaction conditions. For a same or similar catalyst operated at about the same or similar reaction conditions, the RDT may be used to predict when the catalyst is about to transition from linear to non-linear fouling, and the catalyst may be oxidized prior to such transition.

Given that the non-linear fouling portion 140 may correspond to rapid deactivation of the catalyst, it is beneficial to monitor catalyst performance and to oxidize the catalyst prior to reaching the RDT. For example, the catalyst operating temperature may be monitored and the catalyst may be oxidized when the catalyst reaches an operating temperature about equal to or less than the RDT temperature. Where the RDT temperature is represented by a temperature range, the catalyst may be oxidized when the catalyst reaches an operating temperature less than or within the RDT temperature range. In an embodiment, the catalyst is oxidized when the catalyst reaches an operating temperature that is in a range of from the RDT temperature to about 25 degrees Fahrenheit less than the RDT temperature, alternatively from the RDT temperature to about 20 degrees Fahrenheit less than the RDT temperature; alternatively from the RDT temperature to about 15 degrees Fahrenheit less than the RDT temperature; alternatively from the RDT temperature to about 10 degrees Fahrenheit less than the RDT temperature; or alternatively from the RDT temperature to about 5 degrees Fahrenheit less than the RDT temperature.

In addition to or in lieu of monitoring the catalyst operating temperature, the catalyst Time on Stream may also be monitored and the catalyst may be oxidized when the catalyst reaches a Time on Stream about equal to or less than the RDT time. Where the RDT time is represented by a time range, the catalyst may be regenerated when the catalyst reaches a Time on Stream less than or within the RDT time range. Likewise, other catalyst characteristics or properties such as halogen content may be monitored and the catalyst oxidized prior to reaching a value of such characteristic or property that corresponds to the RDT.

Figure 2:
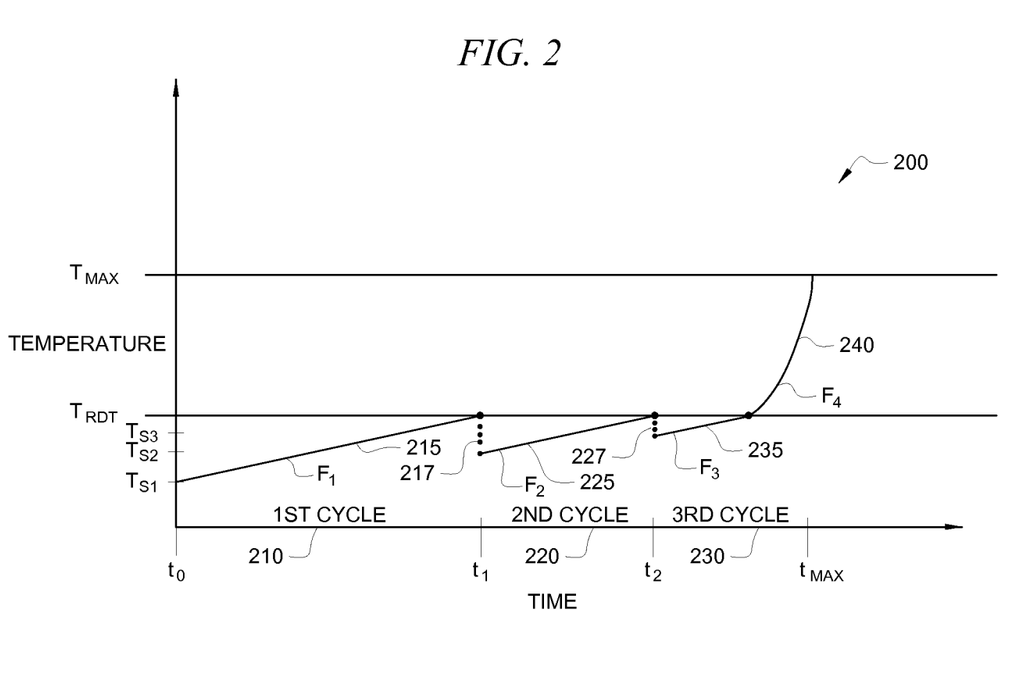
FIG. 2 is graph of a fouling curve where a catalyst is twice regenerated via oxidation prior to reaching a rapid deactivation threshold.

Referring to FIG. 2, a fouling curve 200 is shown for the life of a catalyst having three activity cycles 210, 220, and 230 and 2 regenerations 217 and 227, where the regenerations occur when the catalyst operating temperature is about equal to the RDT temperature ($T_{RDT}$). The first activity cycle 210 begins with fresh catalyst at a Time on Stream of zero and lasts for many months, and during this cycle the activity of the catalyst decreases as evidenced by an increase in the catalyst operating temperature from a first starting temperature, $T_{S1}$. The fouling curve 200 comprises a first activity cycle 210, which further comprises a first linear portion 215 ($1^{st}$ cycle), wherein the slope is about constant, i.e., the fouling rate $F_1$ of the catalyst is about constant. The catalyst operating temperature continues to increase until it approaches the RDT temperature, at which time the reaction may be stopped and the catalyst may be regenerated, for example by oxidizing the catalyst to remove carbon build-up such as coking. During the regeneration, carbonaceous deposits may be removed from the catalytic reactor system and the catalyst contained therein via oxidation thereof, as is described in more detail herein. The regeneration of the catalytic reactor system provides renewed activity to the catalyst (e.g., a second activity cycle 220) as evinced by a lower second cycle starting catalyst operating temperature ($T_{S2}$), which is shown by the vertical drop or decreasing step 217 in the graph. However, when a new activity cycle is started, the starting catalyst operating temperature, $T_{S2}$, may be higher than for the previous activity cycle, $T_{S1}$, as is shown by the progressively increasing catalyst operating temperature at the start of each new activity cycle. Where the catalyst activity is not fully restored after each cycle, the catalyst life may be limited by a maximum number of regenerations, such as the two regenerations shown in FIG. 2.

After the first regeneration, the reaction may be restarted at time $t_1$ with the catalyst operating at a second starting temperature $T_{S2}$. The resultant fouling curve 200 comprises a second activity cycle 220 further comprising a linear portion 225 ($2^{nd}$ cycle), wherein the slope is about constant, i.e., the fouling rate $F_2$ of the catalyst is about constant. The fouling rate $F_2$ may be about equal to or greater than the fouling rate $F_1$, provided however that both $F_1$ and $F_2$ are about constant. Again, the catalyst operating temperature continues to increase until it approaches the RDT temperature ($T_{RDT}$), at which time the reaction may be stopped and the catalyst may be regenerated a second time, for example by oxidation. The regeneration of the catalytic reactor system provides renewed activity to the catalyst (e.g., a third activity cycle 230) as evinced by a lower third cycle starting catalyst operating temperature, $T_{S3}$, which is shown by the vertical drop or decreasing step 227 in the graph.

After the second regeneration, the reaction may be restarted at time $t_2$ with the catalyst operating at a third starting temperature, $T_{S3}$. The resultant fouling curve 200 comprises a third linear portion 235 ($3^{rd}$ cycle), wherein the slope is about constant, i.e., the fouling rate $F_3$ of the catalyst is about constant. The fouling rate $F_3$ may be about equal to or greater than the fouling rate $F_1$ and/or $F_2$, provided however that each of $F_1$, $F_2$, and $F_3$ are about constant. Again, the catalyst operating temperature continues to increase until it approaches the RDT temperature, at which time the reaction may be stopped and the catalyst may be regenerated again. The catalyst may continue to be used and regenerated until the resultant activity cycles are no longer economically efficient. For example, as the starting temperatures ($T_{S1}$, $T_{S2}$, $T_{S3}$, etc.) approach the RDT temperature, the cycle time will continue to decrease until the cycle time is no longer of sufficient duration to warrant continued regeneration cycles based upon the expense of the regeneration and the overall process economics.

When the catalyst is in its final life cycle and will not be regenerated, the reaction is continued and the catalyst operating temperature is allowed to exceed the RDT temperature. The resultant fouling curve comprises a non-linear portion 240, wherein the slope is changing, i.e., the fouling rate $F_4$ of the catalyst is increasing. Non-linear portion 240 represents a period of rapid catalyst deactivation, wherein the operating temperature of the catalyst rapidly increases until the operating temperature reaches a maximum value, $T_{max}$, at which time the reaction is stopped and the catalyst is spent. The total catalyst life of the spent catalyst is represented by the sum of the Times on Stream for all the activity cycles, which is the total operating time from $t_0$ to $t_{max}$. The spent catalyst may be replaced with fresh catalyst and the process may be continued.

Without intending to be limited by theory, it is believed that regeneration of the catalyst prior to reaching the RDT provides for additional activity cycles displaying linear behavior (i.e., having a constant fouling rate), thereby increasing the total catalyst life. In an embodiment, a catalyst regenerated prior to reaching the RDT as disclosed herein may have about a 100% increase in total catalyst life, alternatively a 200% increase in total catalyst life, alternatively a 300% increase in total catalyst life. Without intending to be limited by theory, the total catalyst life may be increased by postponing the rapid and more permanent deactivation of the catalyst resulting from post-RDT, non-linear fouling. That is, exceeding the RDT may result in irreparable damage to the catalyst such that overall life is shortened.

As noted previously, in an embodiment the catalyst is an aromatization catalyst employed in an aromatization process. The aromatization catalyst may comprise an inorganic support, a Group VIII metal such as platinum, and one or more halides such as fluorine, chlorine, iodine, bromine, or combinations thereof. The inorganic support may be a crystalline aluminosilicate, a zeolite, a L-zeolite, or combinations thereof. In some embodiments, the zeolite may be a large pore zeolite. In other embodiments, the zeolite may be a L-zeolite, for example a potassium L-type zeolite, which refers to L-type zeolites wherein the principal exchangeable cation incorporated in the zeolite is potassium. Type L zeolite is described in U.S. Pat. No. 3,216,789, which is incorporated herein by reference. The zeolites may be bound with a binding agent such as silica, alumina, clays, titania, magnesium oxide, or combinations thereof. The Group VIII metal and one or more halides may be added to the support by known methods such as incipient wetness or ion exchange impregnation. In an embodiment, the catalyst comprises a silica bound potassium L-type zeolite support, platinum, chloride, and fluoride, such catalyst having an RDT temperature range of from about 950 to about 1000° F. and a $T_{max}$ of about 1025° F. The amount of platinum in the catalyst may range from about 0.1 to about 5.0% by weight, alternatively from about 0.3 to about 1.5% by weight. The amount of halide in the catalyst may range from about 0.05 to about 5.0% by weight. An example of a suitable commercially available aromatization catalyst is the Aromax® II catalyst available from Chevron Phillips Chemical Company, LP of The Woodlands, Tex. Suitable aromatization catalysts are also disclosed in U.S. Pat. Nos. 7,153,801 and 6,812,180, each of which is incorporated herein by reference in its entirety.

Again, without intending to be limited by theory, the deactivation mechanism for an aromatization catalyst comprising platinum and one or more halides on an inorganic support may be classified into three main categories: carbonaceous deposits (e.g., coking), platinum sintering, and loss of halides. Without wishing to be limited by theory, it is believed that the initial deactivation in the linear fouling portion of the fouling curve is mainly due to carbonaceous deposition on the catalyst. Consequently, due to the deactivation, the reactor temperature has to be increased in order to maintain a constant product yield. As the yield adjusted temperature exceeds the RDT temperature, platinum sintering and loss of halides, which are irreversible via simple oxidation, start to become prominent in the deactivation mechanism. As a result, the deactivation rate increases and the resultant fouling curve display a non-linear deactivation portion. The increased deactivation caused by platinum sintering and loss of halides in the non-linear portion also facilitates the process of carbonaceous deposition on the catalyst. Since all three of the deactivation mechanisms are present in a significant manner and facilitate each other in the non-linear portion, the deactivation rate is observed to accelerate at an increasing rate at the end of the catalyst life.

Without wishing to be limited by theory, it is further believed that the catalyst deactivation mechanism in the linear portion of the fouling curve is dominated by carbonaceous deposition, while the mechanism in the non-linear portion is dominated by platinum sintering and halide loss. Since regeneration via oxidation can only reverse, or partially reverse, the deactivation caused by carbonaceous deposition, regeneration via controlled oxidation may be carried out in the linear portion of the fouling curve prior to substantial deactivation from irreversible platinum sintering and halide loss. Furthermore, compared to the catalyst in the early linear portion, the amount of carbon formed on the catalyst in the late linear portion is increased. Therefore, regeneration of the catalyst via controlled oxidation may be conducted in the late linear portion, i.e., about equal to the RDT temperature, to achieve the economically optimal result. Regeneration via oxidation at or near the RDT temperature decreases the temperature of the reactor necessary to maintain a constant product yield and repositions the catalytic activity from the end of the linear portion back to an earlier stage of the linear portion, as shown in FIG. 2. Repeating the regeneration via oxidation just before the catalyst enters into the non-linear portion of the fouling curve can maintain a lower temperature in the reactor necessary to maintain a constant product yield, reduce or delay the onset of the deactivation caused by platinum sintering and halide loss, and therefore extend the life of the aromatization catalyst. Additionally, maintaining a lower reactor temperature can also reduce the cracking products and improve the selectivity for the aromatics yield.

Any suitable reactor configuration and associated processing equipment may be used to carry out the aromatization process. In various embodiments, the aromatization process may comprise a fixed bed system, a moving bed system, a fluidized bed system, or combinations thereof. The aromatization process may be batch or continuous. In an embodiment, the aromatization process is a fixed bed system comprising one or more fixed bed reactors in series. The flow of the feed to such a system can be upward, downward, or radial through the reactors. "Reactor" and "aromatization reactor" as used herein refer interchangeably to the reactor vessel, reactor internals, and associated processing equipment, including but not limited to the catalyst, inert packing materials, scallops, flow distributors, center pipes, reactor ports, catalyst transfer and distribution system, furnace means, heat transfer means, and piping. Within the aromatization reactor, a hydrocarbon feed is contacted with an aromatization catalyst under reaction conditions (e.g., temperature, flow, and pressure) suitable for aromatization of one or more components in the feed.

"Aromatization" as used herein refers to reforming, or treatment of a hydrocarbon feed to provide an aromatics enriched product (i.e., a product whose aromatics content is greater than in the feed). Typically, one or more components of the feed undergo one or more reforming reactions to produce aromatics. Some of the hydrocarbon reactions that may occur during the reforming operation include the dehydrogenation of cyclohexanes to aromatics, dehydroisomerization of alkylcyclopentanes to aromatics, and dehydrocyclization of acyclic hydrocarbons to aromatics. A number of other side reactions may also occur, including the dealkylation of alkylbenzenes, isomerization of paraffins, and hydrocracking reactions that produce light gaseous hydrocarbons, e.g., methane, ethane, propane and butane.

In embodiments, the feed to the aromatization reactor comprises any combination of those hydrocarbons having from about five ($C_5$) to about nine carbon atoms ($C_9$). In certain embodiments, the feed comprises a naphtha. Such a naphtha feed may be a light hydrocarbon, with a boiling range of about 70° F. to 450° F. The naphtha feed may contain aliphatic or paraffinic hydrocarbons. These aliphatics are converted, at least in part, to aromatics in the reforming reactor system. In an embodiment, the feed is substantially free of sulfur, nitrogen, metals, and other known catalyst poisons. These catalyst poisons can be removed by first using conventional hydrofining techniques, then using sorbents to remove the remaining sulfur compounds. While catalytic reforming typically refers to the conversion of naphtha, other feedstocks can be treated as well to provide an aromatics enriched product. Therefore, while the conversion of naphtha is one embodiment, the present disclosure can be useful for the conversion or aromatization of a variety of feedstocks such as paraffin hydrocarbons, olefin hydrocarbons, acetylene hydrocarbons, cyclic paraffin hydrocarbons, cyclic olefin hydrocarbons, and mixtures thereof, and particularly saturated hydrocarbons.

Operating ranges for a typical reforming process, such as an aromatization process, include catalyst operating temperatures between 700° F. and 1050° F.; a system pressure between 0 and 400 psig; a recycle hydrogen rate sufficient to yield a hydrogen to hydrocarbon mole ratio for the feed to the reforming reactor zone between 0.1 and 20; and a liquid hourly space velocity for the hydrocarbon feed over the reforming catalyst of between 0.1 and 10. Suitable reforming temperatures are achieved by heating the furnace tubes to high temperatures that can range from 700° F. to 1800° F.

As noted previously, the catalyst may be regenerated at least once via oxidation to remove carbonaceous deposits from the catalyst. The catalyst may be removed from the reactor for regeneration. Alternatively, the catalyst may be regenerated in situ within the reactor. In the following discussion, re-oxidation will focus on an in situ oxidation of the catalyst within a reactor system, with the further understanding that reactor system refers to any suitable reactor configuration, including but not limited to one or more fixed bed, radial flow reactors in series. It should be further understood that where multiple reactors are employed, the reactor system may refer to the reactors individually, to the reactors as a whole, or both, as will be apparent to those skilled in the art. Finally, the oxidation procedure is described in the context of an aromatization catalyst and process, with the understanding that such procedure may be tailored and applied to other catalysts and processes as will be apparent to those skilled in the art.

To begin preparations for oxidation of the catalyst, the aromatization reaction may be stopped by first reducing the catalyst temperature and then cutting the hydrocarbon feed to the reactor system. The temperature and feed rate may be reduced incrementally, first the temperature and then feed, until the temperature is in the range of about 600° F. to about 700° F. prior to cutting the feed entirely.

After the reactor system feed has been shut off, residual hydrocarbons may be purged from the reactor system, such as via a purge gas fed to the reactor system. In embodiments, suitable purge gases may comprise gases that are inert under the conditions in the aromatization reactor system. In certain embodiments, suitable purge gases comprise hydrogen, methane, nitrogen, noble gases, or combinations thereof. In an embodiment, a hydrogen recycle stream from within the reactor system is used to purge the reactor system. In some embodiments, the reactor system may or may not be gradually depressured to from about 15 psig to about 45 psig, while maintaining at least about an 80 vol % hydrogen recycle content. The hydrogen recycle may be continued for at least about 4 hours or until the rate of accumulation of liquids in knock-out drums downstream of the reactor(s) drops to below about 5 gallons/hour. Alternatively, the hydrogen recycle/purge may be continued until the accumulation rate is less than about 1 gallon/hour.

Additional steps that may further isolate and purge the reactor system comprise draining low points in the system, employing plant blinds to isolate the system, or in some embodiments, a second purge may be carried out. Suitable gases for a second purge include nitrogen, noble gases, or combinations thereof. In an embodiment, following an initial hydrogen purge of the reactor system or a second purge, condensable hydrocarbons in the reactor system may be further reduced by pressurizing the system to about 15 psig using nitrogen. Purging of the reactor system may continue until combustibles are reduced to less than 2 percent by weight in the recycle gas. In some embodiments, the nitrogen purge is continued until at least an about 90 vol % nitrogen atmosphere in the reactor system is attained.

After purging, oxygen may be fed to the reactor system under suitable reaction conditions such that carbonaceous deposits on the aromatization catalyst are oxidized and thereby removed. The oxygen may be fed to the reactor system via one or more streams comprising air, diluted air, oxygen, diluted oxygen, or combinations thereof. Where multiple reactors are present in the reactor system, the oxygen may be fed to the first reactor and allowed to pass sequentially through the reactor train and/or may be fed to one or more of the reactors individually or even simultaneously.

Various process parameters may be regulated to control the oxidation reaction such as the amount of oxygen in the feed to the reactor system, the reaction temperature, the reaction pressure, and the oxidation time. In embodiments, the concentration of oxygen maintained in the feed stream to the reactor system is about 0.01 to about 10 vol % oxygen; alternatively, about 0.1 to about 5 vol % oxygen; alternatively, about 0.2 to about 0.8 vol % oxygen. In embodiments where air is used as an oxygen feed, the air may be diluted with nitrogen to provide a feed stream having an air to nitrogen (air:$N_2$) ratio of from about 1:1999 to about 1:1; alternatively, about 1:199 to about 1:3; or alternatively, about 1:99 to about 1:24. The reaction temperature may range from about ambient to about 1000° F.; alternatively, from about 300° F. to about 900° F.; or alternatively, from about 425° F. to about 800° F. The reaction pressure may range from about ambient to about 250 psig; alternatively, from about ambient to about 150 psig; or alternatively, from about ambient to about 50 psig. The oxidation time may range from about 1 to about 48 hours; alternatively from about 4 to about 36 hours; or alternatively, from about 8 to about 24 hours.

During the oxidation, the concentration of water in an output stream from the reactor system may be monitored. Oxidation reaction temperatures, temperature ramp rates, and oxygen levels may be adjusted in order to regulate the level of water in the output stream. In embodiments, a suitable water concentration in the output stream during the oxidation operation is less than about 2000 ppm; alternatively, less than about 1500 ppm; or alternatively, less than about 500 ppm.

There may be a large exotherm in the reactor system from oxidation of carbonaceous deposits as the oxidation runs its course. In embodiments, the exotherm is regulated by reducing air injection, by reducing furnace temperatures, by injecting nitrogen, or combinations thereof. In certain embodiments, the exotherm is maintained at less than about 175° F.; alternatively, less than about 150° F.; or alternatively, less than about 125° F.

Oxygen levels in an output stream from the reactor system, also referred to as oxygen breakthrough, may be indicative of the progress toward completion of the oxidation of the carbonaceous deposits and thus completion of the catalyst regeneration. In the beginning of the oxidation, a greater amount of the oxygen fed to the reactor system is consumed in oxidizing the carbonaceous deposits on the catalyst. As the oxidation proceeds, however, the amount of oxygen consumed in the reactor system decreases as the amount of carbonaceous deposits likewise decrease. Accordingly, as the oxidation proceeds, the amount of oxygen in the output stream from the reactor system may increase. The oxidation may be considered sufficiently complete as the concentration of oxygen in the output stream from the reactor system approaches the oxygen concentration in the feed stream to the reactor system. For example, the oxidation may be considered complete from a practical consideration when the oxygen concentration in the output stream becomes about constant over a period of time, and is about equal to or within an acceptably close tolerance to the oxygen concentration in the feed stream, or both.

Upon an indication that the oxidation is complete, the oxidation process may be stopped by halting the oxygen feed to the reactor system. The reactor system may then undergo further steps to prepare the reactor system for start-up of the aromatization process. For example, the reactor system may be purged and the aromatization catalyst therein may be reduced in a reducing atmosphere. The aromatization process may be started by introducing a hydrocarbon feed to the regenerated aromatization catalyst under suitable reaction conditions for aromatization of the hydrocarbon feed. Upon startup of the aromatization process, the regenerated catalyst will once again be operating in a linear portion of the fouling curve as described herein.

EXAMPLES

The method for characterizing and extending the life of an aromatization catalyst by identification of a RDT having been generally described, the following examples are given as a particular embodiment of the method disclosed and to demonstrate a number of the practices and advantages thereof. It is understood that the examples are given as a more detailed demonstration of some aspects of the methods described above, and is not intended to limit the specification or the claims to follow in any manner.

Figure 3:
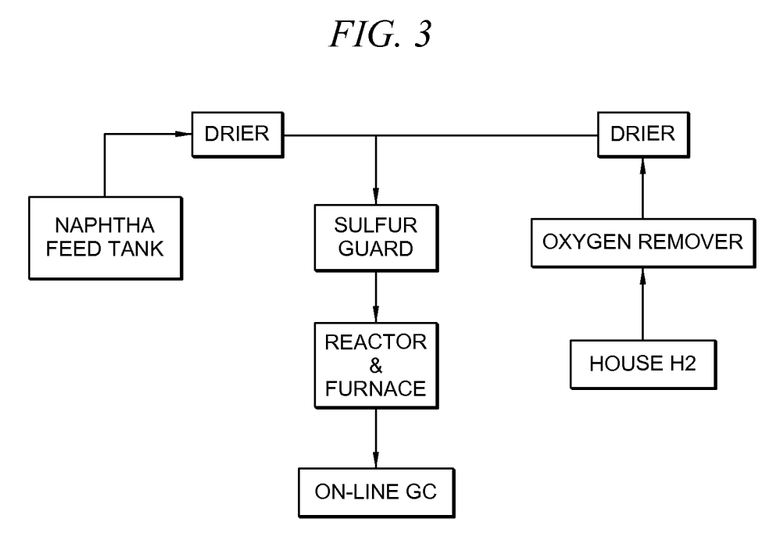
FIG. 3 is a process flow diagram for a laboratory scale reactor system.

Samples of an aromatization catalyst taken at various on stream times in a commercial run were evaluated in the laboratory by accelerated fouling. The aromatization catalyst was a silica bound potassium L-type zeolite support comprising platinum, chloride, and fluoride. The samples were subjected to accelerated fouling conditions in a lab-scale test unit having a simplified process flow as shown in FIG. 3 and operated at 3.0 liquid hourly space velocity (LHSV); 140 psig; 0.5 $H_2$/hydrocarbon feed ratio; and 84% aromatics yield. Carbon levels of the catalysts were determined by elemental analysis using the Carlo Erba elemental analyzer. Chloride and fluoride levels were determined by X-ray fluorescence spectroscopy. Surface area data were obtained by micropore analysis.

Following the accelerated fouling, controlled air oxidation of the fouled catalyst samples were conducted at 900° F. for two hours with an air/$N_2$ ratio of 1:10 to produce a regenerated catalyst. The catalyst was heated in the presence of oxygen under conditions suitable to control exotherms and prevent runaway of the reaction. Such conditions are known to one of ordinary skill in the art.

Example 1

Catalyst sample 1, which was taken from a first batch of catalyst, Batch A, that had not been run commercially, was fouled under accelerated conditions, and a complete fouling curve is shown in FIG. 4. In the yield adjusted temperature range between 980° F. and 990° F., the slope of the fouling curve changes. The change in the slope indicates that the deactivation has evolved from a linear to a non-linear portion of the curve. A turning point at 970° F. is also observed on the catalyst fouling curve. However, the turning point is not related to the nature of the catalyst fouling, but associated with the deactivation caused by a sudden pressure loss of the unit.

Example 2

Figure 5:
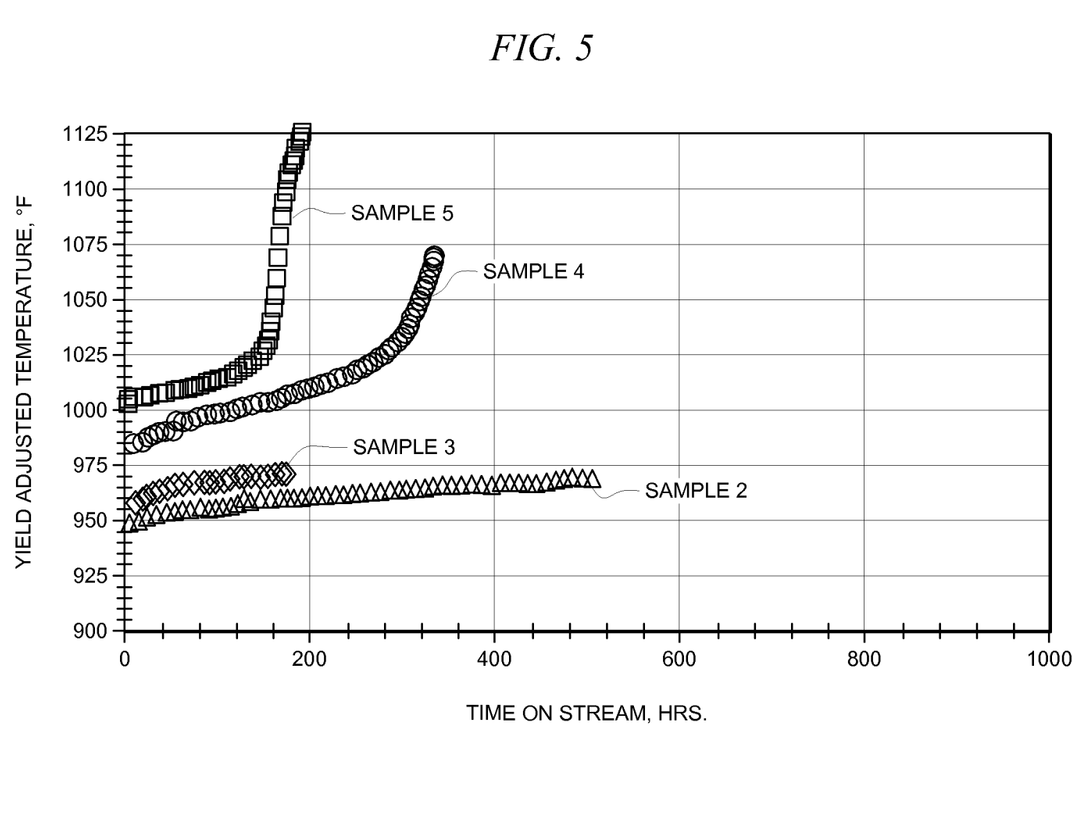

Catalyst samples 2-5 were obtained from a commercial reactor after having been on-line for 9 months (mid-run), 10 months (mid-run), 13 months (mid-run), and 17 months (end-run), respectively. The percent carbon level for each sample, as determined by elemental analysis using the Carlo Erba elemental analyzer, is reported in Table 1. Catalyst samples 2-5 were fouled under accelerated conditions in a lab-scale test reactor and fouling curves for each are shown in FIG. 5. The AFC catalytic properties of the catalyst samples 1-5 are summarized in Table 2. Both the start of run (t-SOR) temperature and fouling rate (t-FR) increase from the 9-month-old catalyst to the 17-month-old catalyst. This trend shows the gradual deactivation of the catalyst with the commercial time on stream (TOS), or catalyst age. The t-SOR temperature for the 13-month-old catalyst of sample 4 is 986° F., which is in the transition range between 980° F. and 990° F. separating the linear and non-linear deactivation regimes as shown in FIG. 4. This observation indicates that the 13-month-old catalyst of sample 4 is about to enter the non-linear deactivation regime. Sample 4 also has a higher carbon content compared to the catalyst samples 2 and 3 taken at earlier points in the commercial run. Therefore, sample 4 should be a good candidate for carbon removal by controlled air oxidation, as will be shown in Example 3.

TABLE 1

Carbon levels of commercial aged catalyst samples

| Catalyst | Carbon (Wt. %) |
| --- | --- |
| Sample 1 (fresh) | <0.01 |
| Sample 2 (9 months) | 0.50 |
| Sample 3 (10 months) | 0.70 |
| Sample 4 (13 months) | 1.34 |
| Sample 5 (17 months) | 2.13 |

TABLE 2

AFC reactor test catalyst properties for commercial aged catalyst samples

| Catalyst | t-SOR Temp. (° F.) | t-FR, (° F./hr) | t-TOS (hrs) |
| --- | --- | --- | --- |
| Sample 1 | 944 | 0.028 | 1633 |
| Sample 2 (9 months) | 953 | 0.035 | ND[1] |
| Sample 3 (10 months) | 963 | 0.049 | ND |
| Sample 4 (13 months) | 986 | 0.116 | 268 |
| Sample 5 (17 months) | 1004 | 0.104 | 131 |

[1]not determined

Example 3

Figure 6:
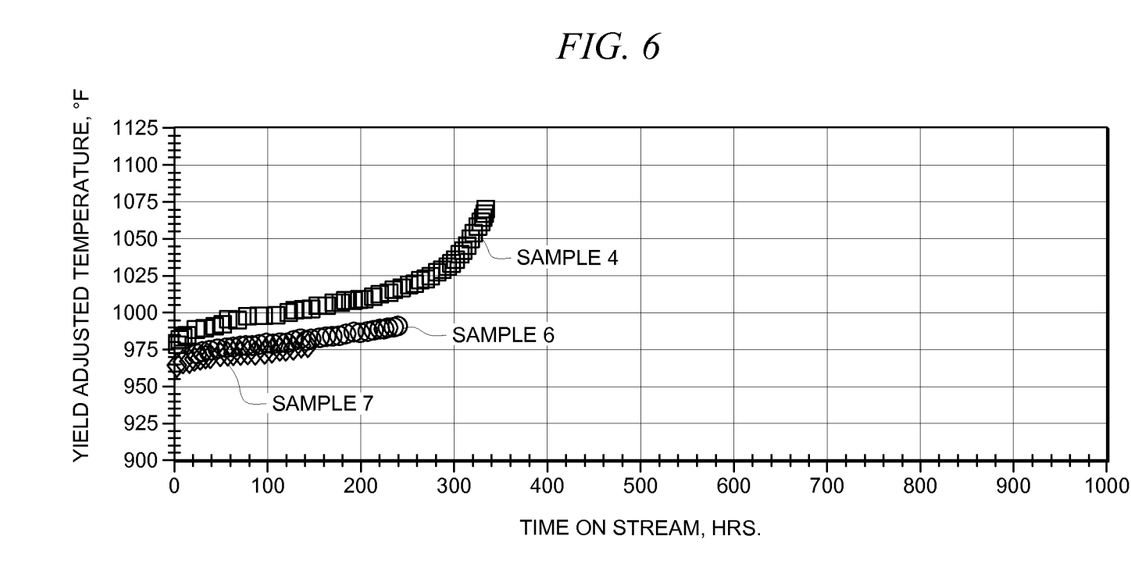

Samples 6 and 7 were prepared by oxidizing two separate portions of Sample 4 (13-month-old catalyst) at 900° F. for two hours with an air/$N_2$ ratio of 1:10. In order to confirm the oxidation conditions, samples 6 and 7 were oxidized under the same conditions, but in different batches. The oxidized samples 6 and 7 catalyst properties were evaluated respectively in two different lab AFC reactor units, A and B, and the resultant fouling curves are shown in FIG. 6 along with the sample 4 result for comparison. A summary of the catalytic properties and carbon content in the original catalyst and oxidized catalysts is listed in Table 3. Compared to the original 13-month-old catalyst, both the t-SOR and t-FR of the oxidized catalysts are improved. Compared with sample 4, about 80% of the carbon has been removed from samples 6 and 7 by air oxidation. The carbon removal results in the regeneration of the catalytic properties and a return to the linear portion of the fouling curve since the sample 6 and 7 t-SOR temperatures are less than the RDT.

TABLE 3

| Catalyst | t-SOR Temp (° F.) | t-FR (° F./hr) | Carbon (wt. %)[1] |
|---|---|---|---|
| Sample 4 (13 months) non-oxidized | 986 | 0.116 | 1.34 |
| Sample 6 (13 months) oxidized at 900° F.; unit A | 974 | 0.053 | 0.27 |
| Sample 7 (13 months) oxidized at 900° F.; unit B | 968 | 0.065 | 0.36 |

[1]These are pre-lab reactor test carbon amounts.

Example 4

Samples 8 and 9 were obtained by taking portions from sample 4 (i.e., the 13-month-old catalyst) and oxidizing them separately at 700° F. and 800° F., respectively, for two hours with an air/$N_2$ ratio of 1:10 using the same conditions described earlier to control the exotherm. The carbon content of samples 6, 8, and 9 are listed in Table 4. Compared with the oxidation at 900° F., the carbon removal at 800° F. and especially at 700° F. is less effective.

TABLE 4

| Catalyst Information | Carbon Amt. (Wt. %) |
|---|---|
| Sample 6 (13 months) Oxidized at 900° F. | 0.27 |
| Sample 8 (13 months). Oxidized at 800° F. | 0.65 |
| Sample 9 (13 months). Oxidized at 700° F. | 0.87 |

Example 5

Sample 10 was prepared by oxidizing a portion from sample 3 (i.e., the 10-month-old catalyst) at 900° F. for two hours with an air/$N_2$ ratio of 1:10. Sample 11 was prepared by oxidizing a portion from sample 5 (i.e., the 17-month-old catalyst) at 900° F. for two hours with an air/$N_2$ ratio of 1:10. A portion of each oxidized sample was analyzed for wt % carbon, while another portion of each oxidized sample was evaluated in a lab-scale unit by accelerated fouling. The results are listed in Table 5.

TABLE 5

| Catalyst Information | t-SOR (° F.) | t-FR (° F./hr) | t-TOS (hrs) | Carbon Amt. (w. %)[1] |
|---|---|---|---|---|
| Sample 5 (17 months) Non-oxidized | 1004 | 0.104 | 131 | 2.13 |
| Sample 11 (17 months) Oxidized at 900° F. | 985 | 0.175 | 159 | 0.50 |
| Sample 3 (10 months) Non-oxidized | 963 | 0.049 | ND[2] | 0.70 |
| Sample 10 (10 months) Oxidized at 900° F. | 962 | 0.048 | ND | 0.32 |
| Sample 2 (9 months) Non-oxidized | 953 | 0.035 | ND | 0.50 |

[1]These are pre-lab reactor test carbon amounts.
[2]not determined

The t-SOR temperature of sample 5 (17-month-old catalyst) is 1004° F./hour. Compared to the transition RDT temperature range of from about 980° F. to about 990° F. in the fouling curve of sample 1 (fresh catalyst), sample 5 (17-month-old catalyst) is already in the non-linear regime. After the air oxidation process, the t-SOR temperature of sample 11 decreases by 19° F. However, this t-SOR temperature is barely back down to the RDT and additionally the fouling rate is not improved after the air oxidation. As a result, the total length of the catalyst life (i.e. t-TOS) is not extended greatly, i.e., 159 hours for sample 11 versus 131 hours for sample 5. The failure to reduce fouling rate or significantly extend catalyst life may be explained by the fact that sample 5 was taken at the end of the run and was already in the non-linear portion of the fouling curve prior to the oxidation.

In contrast, the t-SOR temperature of sample 3 (10-month-old catalyst) is 963° F., which is far below the transition t-RDT temperature range (980-990° F.) separating the linear and non-linear portions of the fouling curve. As a result, the controlled air oxidation treatment provides little improvement of the catalytic performance of sample 10 in comparison to sample 3, which may be explained by relatively low carbon build up on the 10-month-old catalyst. Therefore, the restoration of the catalytic properties by carbon removal via oxidation for this catalyst is minor. During the air oxidation the platinum may sinter minimally, which may further offset the gain from air oxidation. Sample 2 (9-month-old catalyst) was on-line an even shorter time than sample 3 (10-month-old catalyst), and thus has a lower t-SOR temperature (953° F.). Therefore, sample 2 was not considered for the air oxidation treatment.

Example 6

Catalyst sample 12, which was fresh catalyst taken from a second batch of catalyst Batch B, was fouled under accelerated conditions, and a complete fouling curve is shown in FIG. 7. The fouling curve for sample 12 is very similar to the fouling curve for sample 1, and each show an RDT temperature transition range between 980° F. and 990° F. After the transition, the catalyst starts to deactivate in a non-linear, accelerated fashion.

Example 7

Catalyst sample 13 was taken at the end of a commercial run of the second catalyst batch, Batch B, from Example 6 and was oxidized as described previously to produce sample 14. Catalyst sample 15 was taken from a third catalyst batch, Batch C, after 12 months in a commercial run and was fouled under accelerated fouling conditions. Catalyst sample 16 was obtained by oxidizing a portion of sample 15 under oxidation conditions described previously. The results for samples 12-16 are listed in Table 6. Sample 13, which was taken at the end of the commercial run, is in the non-linear portion of the fouling curve as evinced by a t-SOR of 1004° F. As expected, the air oxidation of the end-of-run catalyst as shown in sample 13 increased the fouling rate and did not extend the catalyst life.

TABLE 6

| Catalyst | t-SOR (° F.) | t-FR (° F./hr) | t-TOS (hrs) | Carbon (Wt. %)[1] |
|---|---|---|---|---|
| Sample 12 (Fresh second commercial batch) | 950 | 0.065 | 680 | 0.03 |
| Sample 13 (end-run) Non-oxidized | 1004 | 0.104 | 131 | 2.13 |
| Sample 14 (end-run) Oxidized at 900° F. | 957 | 0.204 | 130 | 0.14 |
| Sample 15 (12 months) Non-oxidized | 985 | 0.128 | ND[2] | 1.23 |

TABLE 6-continued

| Catalyst | t-SOR (° F.) | t-FR (° F./hr) | t-TOS (hrs) | Carbon (Wt. %)[1] |
|---|---|---|---|---|
| Sample 16 (12 months) Oxidized at 900° F. | 970 | 0.060 | ND | 0.33 |

[1]These are pre-lab reactor test carbon amounts.
[2]not determined

Figure 8:
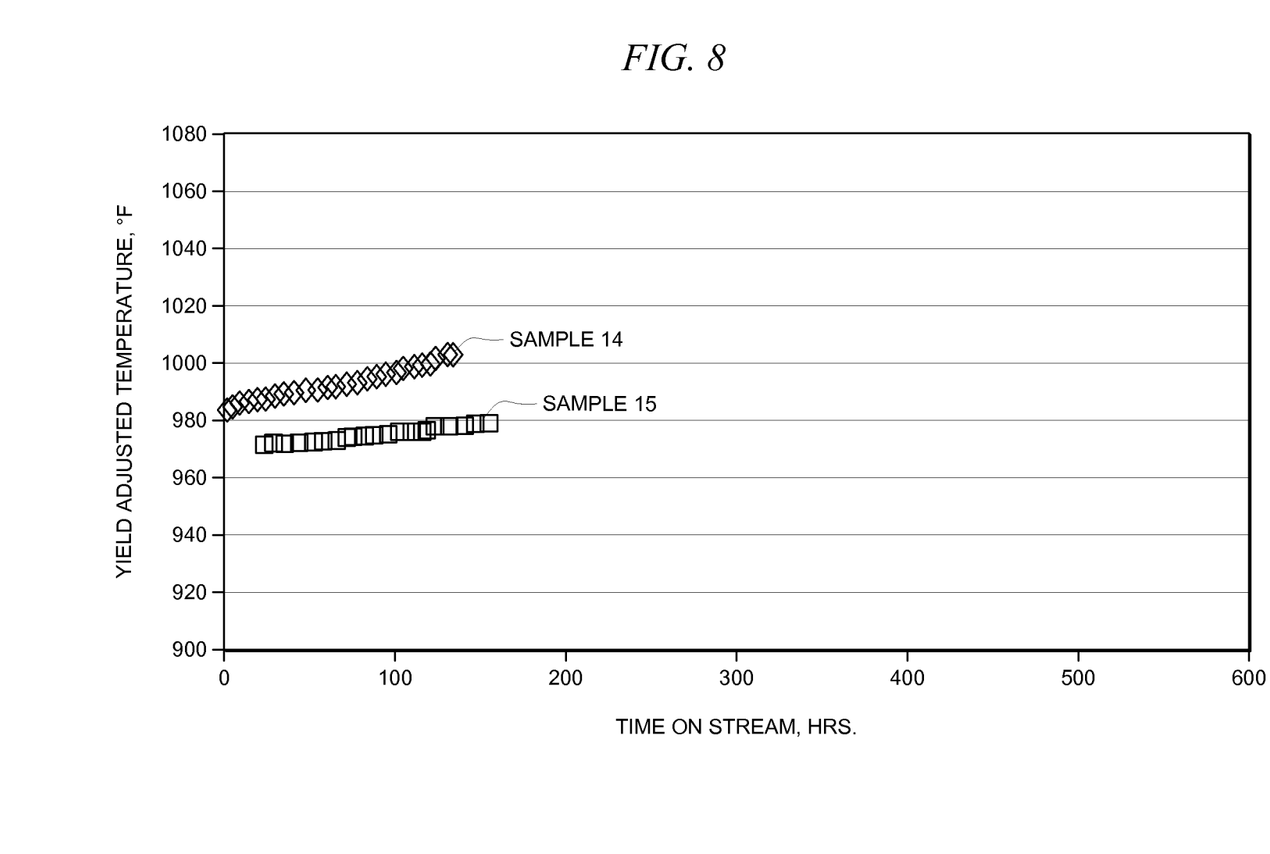

The t-SOR temperature of sample 15 is 985° F., which indicates that sample 15 is in the t-RDT temperature transition range and about to enter the non-linear portion of the fouling curve. Thus, regeneration of this catalyst by air oxidation should be effective, as such is being performed after significant carbonaceous deposits may have formed but prior to the t-RDT threshold. Compared to sample 15, the t-SOR temperature of the oxidized catalyst of sample 16 is decreased by 15° F. and its fouling rate is reduced to half. After the air oxidation, the amount of carbon on the catalyst is reduced by approximately 75%. The fouling curves of the samples 13, 15 and 16 are in the non-linear portion of the fouling curve, as is shown in FIG. 8. Without wishing to be limited by theory, it is believed that the improvement in the catalytic performance in sample 16 may be attributed to carbon removal on the catalyst via oxidation just prior to the non-linear portion of the fouling curve. Sample 15 may not have experienced the same level of reduction in the t-SOR as the sample was subjected to the disclosed procedure after having passed the t-RDT.

Overall, the Examples show that the life of an aromatization catalyst may be extended by controlled air oxidation of the catalysts, and in particular oxidation of the catalysts when they are about to reach the temperature range transitioning from a linear to a non-linear portion of the fouling curve.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims that follow, that scope including all equivalents of the subject matter of the claims. Each and every claim is incorporated into the specification as an embodiment of the present invention. Thus, the claims are a further description and are an addition to the preferred embodiments of the present invention. The discussion of a reference herein is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A method of aromatizing a hydrocarbon comprising:
    contacting the hydrocarbon with an aromatization catalyst comprising a crystalline aluminosilicate within a commercial-scale aromatization reactor to produce aromatic hydrocarbons;
    identifying a rapid deactivation threshold (RDT) for the catalyst, wherein identifying the RDT comprises identifying a point or range at which a fouling rate of the catalyst as a function of Time on Stream becomes non-linear, identifying a point or range at which a fouling rate of the catalyst as a function of a reactor temperature becomes non-linear, identifying a point or range at which a fouling rate of the catalyst as a function of a halogen content of the catalyst becomes non-linear, or identifying a critical amount of halogen required in the catalyst to inhibit catalyst deactivation during aromatization; and
    operating the aromatization reactor comprising the catalyst to extend the Time on Stream of the reactor prior to reaching the RDT.

2. The method of claim 1 wherein operating the reactor to extend the Time on Stream further comprises oxidizing the catalyst prior to reaching the RDT.

3. The method of claim 1 wherein the catalyst comprises an L-zeolite;
    platinum; and a halide that is chloride, fluoride or mixtures thereof, and wherein the hydrocarbon comprises naphtha.

4. The method of claim 1 wherein the catalyst is oxidized in situ within the reactor.

5. A method of aromatizing a hydrocarbon comprising:
    identifying a rapid deactivation threshold (RDT) of an aromatization catalyst comprising a crystalline aluminosilicate, wherein identifying the RDT comprises identifying a point or range at which a fouling rate of the catalyst as a function of Time on Stream becomes non-linear, identifying a point or range at which a fouling rate of the catalyst as a function of a reactor temperature becomes non-linear, identifying a point or range at which a fouling rate of the catalyst as a function of a halogen content of the catalyst becomes non-linear, or identifying a critical amount of halogen required in the catalyst to inhibit catalyst deactivation during aromatization; and
    contacting the hydrocarbon with the aromatization catalyst within a commercial-scale aromatization reactor to produce aromatic hydrocarbons.

6. The method of claim 5 wherein identifying the RDT further comprises employing the catalyst in a reactor under an accelerated fouling condition on a test reactor system to identify a test rapid deactivation threshold (t-RDT).

7. The method of claim 6 further comprising predicting the RDT for the commercial-scale aromatization reactor based upon the t-RDT.

8. The method of claim 7 wherein the catalyst is oxidized in situ in response to the RDT predicted by the t-RDT.

9. The method of claim 8 wherein the oxidation extends the Time on Stream of the catalyst within the commercial-scale aromatization reactor by at least about 100%.

10. The method of claim 6 wherein the accelerated fouling condition comprises an elevated pressure, a decrease in a hydrogen to hydrocarbon mole ratio, an elevated hydrocarbon flow per unit of the catalyst, or any combination thereof.

11. The method of claim 6 wherein the catalyst is removed from the commercial-scale aromatization reactor and transferred to the test reactor system to identity the t-RDT under the accelerated fouling condition.

12. The method of claim 5 wherein the catalyst comprises an L-zeolite; platinum; and a halide that is chloride, fluoride or mixtures thereof, and wherein the hydrocarbon comprises naphtha.

13. A method of aromatizing a hydrocarbon comprising:
predicting a rapid deactivation threshold (RDT) for a commercial-scale aromatization reactor by employing the catalyst in a reactor system under an accelerated fouling condition to identify a test rapid deactivation threshold (t-RDT);
predicting the RDT for the commercial-scale aromatization reactor based upon the t-RDT;
contacting a hydrocarbon with the aromatization catalyst within the commercial-scale aromatization reactor to produce aromatic hydrocarbons; and
oxidizing the catalyst in situ within the commercial-scale aromatization reactor prior to the predicted RDT to extend the Time on Stream of the aromatization catalyst,
wherein the catalyst comprises an L-zeolite; platinum; and a halide that is chloride, fluoride or mixtures thereof, and wherein the hydrocarbon comprises naphtha.

* * * * *